US009365818B2

(12) United States Patent
Borody

(10) Patent No.: US 9,365,818 B2
(45) Date of Patent: *Jun. 14, 2016

(54) CULTURE MEDIUM AND A METHOD FOR DETECTION OF PARASITES

(71) Applicant: Thomas Julius Borody, Castle Hill (AU)

(72) Inventor: Thomas Julius Borody, Castle Hill (AU)

(*) Notice: Subject to any disclaimer, the term of this patent is extended or adjusted under 35 U.S.C. 154(b) by 62 days.

This patent is subject to a terminal disclaimer.

(21) Appl. No.: 13/694,488

(22) Filed: Dec. 5, 2012

(65) Prior Publication Data

US 2013/0102026 A1   Apr. 25, 2013

Related U.S. Application Data

(63) Continuation of application No. 10/541,528, filed as application No. PCT/AU2004/000153 on Feb. 10, 2004, now Pat. No. 8,372,599.

(30) Foreign Application Priority Data

Feb. 10, 2003 (AU) ............................ 2003-900553

(51) Int. Cl.
   *C12Q 1/04*   (2006.01)
   *C12N 1/10*   (2006.01)

(52) U.S. Cl.
   CPC .. *C12N 1/10* (2013.01); *C12Q 1/04* (2013.01); *G01N 2333/44* (2013.01)

(58) Field of Classification Search
   None
   See application file for complete search history.

(56) References Cited

U.S. PATENT DOCUMENTS

| 3,071,575 | A * | 1/1963 | Doyle | 540/338 |
| 5,272,058 | A | 12/1993 | Petri | 435/7.22 |
| 5,334,509 | A | 8/1994 | Riordan | 435/37 |
| 8,372,599 | B2 | 2/2013 | Borody | 435/34 |
| 2003/0003527 | A1 | 1/2003 | Shimakita | 435/34 |
| 2006/0115872 | A1 | 6/2006 | Borody | 435/34 |
| 2013/0273583 | A1 | 10/2013 | Borody | 435/12 |

OTHER PUBLICATIONS

Hauck et al. (2010) *Histomonas meleagridis* (Protozoa: Trichomonadidae): Analysis of Growth Requirements In Vitro. J. Parasitol 96(1): 1-7.*
Letter/Written Disclosure of the Supplemental Information Disclosure Statement for the above-referenced application, mailed on Jan. 23, 2013, 2 pages.
"Media for xenic cultivation," [online][retrieved on Dec. 15, 2005] Retrieved from:<URL:homepages.lshtm.ac.uk/entam oeba/xenic. htm [3 pages].
Andrews and Borody, "'Putting back the bugs': bacterial treatment relieves chronic constipation and symptoms of irritable bowel syndrome," Med J Aust. 159(9):633-634 (1993).
Boeck and Drbohlav, "The cultivation of Endamoeba histolytica," American Journal of Hygiene 5:407 (1925).
Borody et al., "Bowel-flora alteration: a potential cure for inflammatory bowel disease and irritable bowel syndrome?" Med J Aust. 150(10):604 (1989).
Borody et al., "Bacteriotherapy using fecal flora: toying with human motions," J Clin Gastroenterol. 38(6):475-483 (2004).
Borody et al., "Eradication of *Dientamoeba fragilis* can resolve IBS-linek symptoms," J. Gastroenterol. Hepatol. 17(Suppl):A103 (202).
Borody et al., "Irritable bowel syndrome and *Dientamoeba fragilis*," IBIS News and Views. 4-5 (2002).
Borody et al., "Treatment of ulcerative colitis using fecal bacteriotherapy," J Clin Gastroenterol. 37(1):42-47 (2003).
Borody T., "'Flora Power'—fecal bacteria cure chronic C. difficile diarrhea," Am J Gastroenterol. 95(11):3028-3029 (2000).
Clark, C., "Riboprinting: a tool for the study of genetic diversity in microorganisms," J. Euk. Microbiol. 44:277-283 (1997).
Clark and Diamond, "Methods for cultivation of parasitic protists of clinical importance," Clinical Microbiology Reviews 15(3):329-341 (2002).
Diamond et al., "Axenic cultivation of *Entamoeba histolytica*," Science 134:336-337 (1961).
Dobell and Laidlaw, "On the cultivation of *Entamoeba histolytica*," Parasitology 18: 283-318 (1926).
Hauck et al., "*Histomonas meleagridis* (Protozoa: Trichomonadidae): analysis of growth requirements in vitro," J Parasitol. 96(1):1-7 (2010).
Johnson et al., "Emerging from obscurity: biological, clinical and diagnostic aspects of *Dientamoeba fragilis*," Clin Microbiol Rev 17:553-570 (2004).
Nakamura, M., Nutrition and physiology of Endamoeba histolytica Bacteriol Rev 17(3):189-212 (1953).
Ockert, G., "Symptomatology, pathology, epidemiology and diagnosis of *Dientamoeba fragilis*," *Trichomonads parasitic in humans*, Hoiberg, B. (Ed.), New York: Springer, pp. 394-410 (1990).
Palomino J., "Peptone-yeast autolysate-fetal bovine serum 10, a simple, inexpensive liquid medium for clutivation of Leishmania," Supp. Journal of Clinical Microbiology 15(5):949-950 (1982).
Robinson et al., "The laboratory diagnosis of human parasitic amoebae," Transactions of the Royal Society of Tropical Medicine and Hygiene 62:285-294 (1968).
Sehgal et al., "Comparison of two media for the isolation and short-term culture of Entamoeba histolytica and E. dispar," Transactions of the Royal Society of Tropical Medicine and Hygiene 89:394 (1995).
Sawangjaroen et al., "Diagnosis by faecal culture of Dientamoeba fragilis in Australian patients with diarrhea," Trans. Roy. Soc. Trop. Med. Hyg. 87:163-1665 (1993).
Visvesvara and Garcia, "Culture of protozoan parasites," Clin Microbiol. Rev. 15(3): 327-328 (2002).
Windsor and Macfarlane, "Irritable bowel syndrome: the need to exclude *Dientamoeba fragilis*," Am J Trop Med Hyg 72:501 (2005).
Windsor and Rafay, "Laboratory detection of Dientamoeba fragilis," Br J Biomed Sci 1997; 54:223-224 (1997).

(Continued)

Primary Examiner — Lisa J Hobbs

(74) Attorney, Agent, or Firm — Dentons US LLP; Stephanie Seidman

(57) ABSTRACT

This invention relates to a culture medium, a kit containing the culture medium and to a method for detection of a parasite such as *Dientamoeba fragilis* and/or another parasite. The culture medium of the invention is bi-phasic and includes a solid phase containing an egg slope or agar slope and a liquid phase containing a serum and a peptone.

11 Claims, 1 Drawing Sheet

(56) References Cited

OTHER PUBLICATIONS

Windsor et al., "*Blastocystis hominis*," Br J Biomed Sci 2001; 58:253.
Windsor et al., "Detection of dientamoeba fragilis and blastocystis hominis using a simple staining method," Br J Biomed Sci 63:27-28 (2006).
Windsor et al., "Detection of *Dientamoeba fragilis* by culture," Br J Biomed Sci 60:79-83 (2003).
Windsor et al., "*Dientamoeba fragilis*: the unflagellated human flagellate. A review," Br J Biomed Sci 56:293-306 (1999).
Windsor et al., "Internal transcribed spacer dimorphism and diversity in *Dientamoeba fragilis*," J Euk Microbiol 53:188-192 (2006).
Windsor et al., "Molecular typing of *Dientamoeba fragilis*," Br J Biomed Sci 61:153-155 (2004).
Windsor et al., "Multiple reproductive processes in *Blastocystis hominis*," Trends Parasitol 19:289 (2003).
Windsor et al., "The incidence of *Blastocystis hominis* in faecal samples submitted for routine microbiological examination," Br J Biomed Sci 59:154-157 (2002).
Windsor et al., "The incidence of *Dientamoeba fragilis* in faecal samples submitted for routine microbiological analysis," Br J Biomed Sci 55:172-175 (1998).
Windsor et al.,"More laboratories should test for *Dientamoeba fragilis* infection," BMJ 318:735 (1998).
Windsor, J., "*Blastocystis hominis*," Chapter 26. *Topley and Wilson's Microbiology and Microbial Infection*. 10$^{th}$ Edition (2005).
International Search Report, issued Mar. 11, 2004, in connection with corresponding International Patent Application No. PCT/AU04/00153, 3 pages.
Written Opinion, issued Mar. 11, 2004, in connection with corresponding International Patent Application No. PCT/AU04/00153, 3 pages.
International Preliminary Report on Patentability, issued Jan. 12, 2005, in connection with corresponding International Patent Application No. PCT/AU04/00153, 3 pages.
Office Action, issued Apr. 3, 2009, in connection with U.S. Appl. No. 10/541,528, 9 pages.
Response to Office Action, issued Apr. 3, 2009, in connection with U.S. Appl. No. 10/541,528, 14 pages.
Final Office Action, issued Oct. 29, 2009, in connection with U.S. Appl. No. 10/541,528, 8 pages.
Request for Continued Examination and Respsonse to Final Office Action, issued Oct. 29, 2009, in connection with U.S. Appl. No. 10/541,528, 10 pages.
Office Action, issued Jan. 24, 2012, in connection with corresponding U.S. Appl. No. 10/541,528, 8 pages.
Response to Office Action, issued Jan. 24, 2012, in connection with corresponding U.S. Appl. No. 10/541,528, 11 pages.
Notice of Allowance, issued Sep. 6, 2012, in connection with corresponding U.S. Appl. No. 10/541,528, 8 pages.
European Search Report, mailed Jun. 23, 2006, in connection with corresponding European Patent Application No. 04709553.4, 2 pages.
Examination Report, mailed May 23, 2006 in connection with corresponding European Patent Application No. 04709553.4, 4 pages.
Response to Examination Report, mailed May 23, 2006 in connection with European Patent Application No. 04709553.4, 10 pages.
Examination Report, mailed Jan. 2, 2008, in connection with corresponding European Patent Application No. 04709553.4, 4 pages.
Response to Examination Report, mailed Jan. 2, 2008, in connection with corresponding European Patent Application No. 04709553.4, 15 pages.
Examination Report, mailed Nov. 2, 2009, in connection with corresponding European Patent Application No. 04709553.4, 4 pages.
Response to Examination Report, mailed Nov. 2, 2009, in connection with corresponding European Patent Application No. 04709553.4, 19 pages.
Examination Report, mailed Aug. 12, 2011, in connection with corresponding European Patent Application No. 04709553.4, 7 pages.
Response to Examination Report, mailed Aug. 12, 2011, in connection with corresponding European Patent Application No. 04709553.4, 13 pages.
Letter/Written Disclosure of the Supplemental Information Disclosure Statement for the above-referenced application, mailed on Apr. 18, 2013, 2 pages.
Letter/Written Disclosure of the Supplemental Information Disclosure Statement for the above-referenced application, submitted Apr. 23, 2014, 2 pages.
Examination Report, mailed Oct. 10, 2013, in connection with European Patent Application No. 04709553.4, 6 pages.
Letter/Written Disclosure of the Supplemental Information Disclosure Statement for the above-referenced application, mailed on Nov. 6, 215, 2 pages.
Office Action, dated Jul. 16, 2010, in connection with Canadian Patent Application No. 2,515,600, 4 pages.
Response, submitted Jan. 17, 2011, to Office Action, dated Jul. 16, 2010, in connection with Canadian Patent Application No. 2,515,600, 8 pages.
Office Action, dated Dec. 9, 2011, in connection With Canadian Patent Application No. 2,515,600, 4 pages.
Response, submitted Jun. 11, 2012, to Office Action, dated Dec. 9, 2011, in connection with Canadian Patent Application No. 2,515,600, 7 pages.
Office Action, dated Nov. 13, 2012, in connection with Canadian Patent Application No. 2,515,600, 2 pages.
Response, submitted May 13, 2013, to Office Action, dated Nov. 13, 2012, in connection with Canadian Patent Application No. 2,515,600, 7 pages.
Office Action, dated Aug. 30, 2013, in connection with Canadian Patent Application No. 2,515,600, 4 pages.
Response, submitted Feb. 28, 2014, to Office Action, dated Aug. 30, 2013, in connection with Canadian Patent Application No. 2,515,600, 22 pages.
Summons to Attend Oral Proceedings Pursuant to Rule 115(1) EPC, dated Jul. 1, 2015, in connection with European Patent Application No. 04709553.4, 6 pages.
Request for Further Processing under Article 121 EPC and Response, submitted Jul. 28, 2014, to Communication Pursuant to Article 94(3), mailed Oct. 10, 2013, in connection with European Patent Application No. 04709553.4, 13 pages.
Office Action, dated Jan. 8, 2015, in connection with Canadian Patent Application No. 2,515,600, 10 pages.
Response, submitted Jul. 8, 2015, to Office Action, dated Jan. 8, 2015, in connection with Canadian Patent Application No. 2,515,600, 21 pages.
Summons to Attend Oral Proceedings Pursuant to Rule 115(1) EPC, dated Aug. 3, 2015, in connection with European Patent Application No. 04709553.4, 1 page.
Letter/Written Disclosure of the Supplemental Information Disclosure Statement for the above-reference application, filed herewith on Mar. 25, 2016, 2 pages.
Decision to refuse a European Patent application, dated Jan. 21, 2016, in connection with European Patent Application No. 04709553.4, 7 pages.

\* cited by examiner

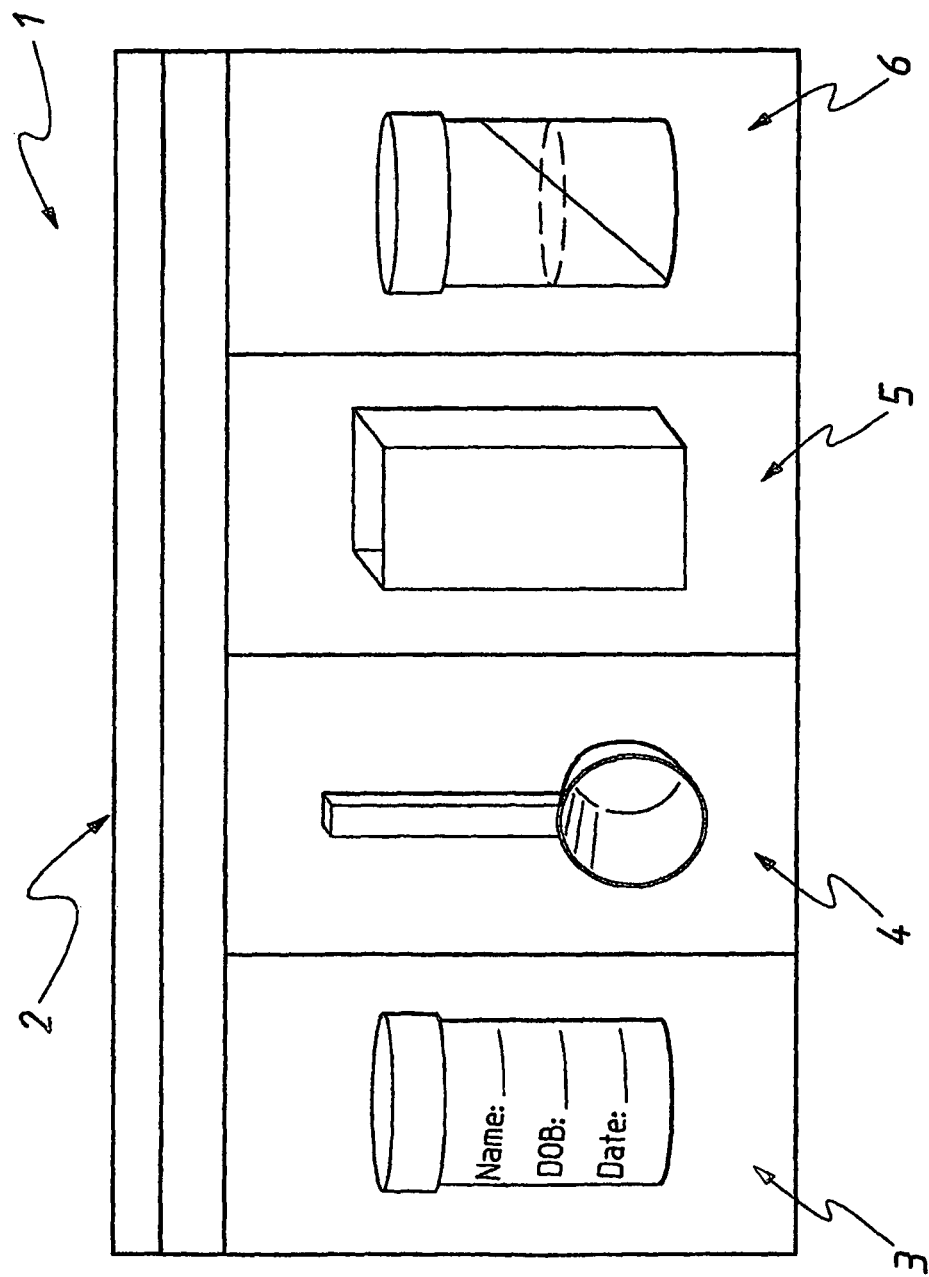

CULTURE MEDIUM AND A METHOD FOR DETECTION OF PARASITES

RELATED APPLICATIONS

This application is a continuation of co-pending allowed U.S. patent application Ser. No. 10/541,528, filed Jul. 7, 2005, which is the U.S. National Stage application of PCT/AU2004/000153, filed Feb. 10, 2004, and entitled "A CULTURE MEDIUM AND A METHOD FOR DETECTION OF PARASITES," which claims benefit of priority to Australian Patent Application Serial No. AU2003-900553, filed on Feb. 10, 2003. The subject matter of each of the-above mentioned applications is incorporated by reference in its entirety.

FIELD OF THE INVENTION

This invention relates to a culture medium, a kit containing the culture medium and to a method for detection of a parasite such as *Dientamoeba fragilis* and/or another parasites.

BACKGROUND

*Dientamoeba fragilis* (*D. fragilis*) is one of the most common parasites affecting animals including humans. It is thought to be spread via pinworms acquired by the faecal/oral route and to reside in the gastrointestinal tract of the host, clinically causing such symptoms as abdominal discomfort, loose motions, bloating, diarrhoea, at times nausea, pruritus ani, malaise and other non-specific symptoms. It is perhaps one of the most common parasites residing in the gastrointestinal tract of individuals in the western world and yet few physicians are aware of its presence and its contribution to disease, chiefly due to the fact that it is not diagnosed frequently.

*Dientamoeba fragilis* is notoriously difficult to diagnose unless suitable fixatives and permanent staining methods are employed and adequately trained personnel are available (Windsor and Johnson 1999—Windsor J J, Johnson E H. *Dientamoeba fragilis*: the unflagellated human flagellate. A review. Br J Biomed Sci 1999; 56:293-306). Culture methods have been shown to be more sensitive than microscopy at times (Ockert 1990, Sawangjaroen 1993—Ockert G., Symptomatology, pathology, epidemiology and diagnosis of *Dientamoeba fragilis*: In: Honiberg B M, ed., Trichomonads parasitic in humans. New York; Springer 1990; 394-410), however these culture methods are not currently used in diagnostic laboratories because of their complexity.

If the methodology could be simplified, culture would be more easy to perform and would have the added advantage that the isolates can be lysed and typed, thus aiding future epidemiological studies on top of simple diagnostic studies. *D. fragilis* does not have a resistant cyst stage and consequently cannot survive outside the human host for longer than 12 hours (Sawangjaroen 1993—Sawangjaroen N, Luke R, Provic P., Diagnosis by faecal culture of *Dientamoeba fragilis* in Australian patients with diarrhoea. Trans Roy Soc Trop Med Hyg 1993; 87:163-5). In order for the culture method to be successful, the culture medium needs to be simple and needs to be one that will support the growth of *D. fragilis* and other parasites, e.g. *Blastocystis hominis*. Furthermore, the medium needs to have the features of long shelf life and transportability. In addition, the detection of the growing parasites needs to be carried out easily by technicians with minimal training. Previous methods have included specific stains, e.g., trichome and iron-haematoxylin, and more recently Riordan (U.S. Pat. No. 5,334,509) has suggested an acridine orange or acridine yellow stain for more specifically detecting *D. fragilis*. However, this method lacks specificity as it merely stains up RNA/DNA and therefore stains numerous parasites, including non-pathogenic ones. Using this method *D. fragilis* is at times indistinguishable microscopically from such parasites, and so the diagnosis again depends on the availability of highly trained microscopists to diagnose *D. fragilis*.

It would also be desirable to simplify the culture medium so that it can be used by an unskilled technician.

SUMMARY OF THE INVENTION

It is the object of the present invention to overcome or substantially ameliorate at least one of the above described disadvantages.

According to a first aspect of the invention, there is provided a bi-phasic culture medium including a solid phase containing an egg slope or agar slope; and a liquid phase including a serum and a peptone.

In one embodiment, the solid phase is an egg slope.
In one embodiment, the serum is horse serum.
In one embodiment, the serum is rabbit serum.
In one embodiment, the peptone is bactopeptone.
In one embodiment, the liquid phase includes a phosphate buffered saline having a pH of from about 6.8 to about 7.8. Suitably the liquid phase contains up to about 98 vol % of the phosphate buffered saline, about 1 to about 15 vol % of the serum, and about 1 to about 15 vol % of bactopeptone (about 1 to about 40 w/w), in the liquid phase. The medium may also include an antibiotic from the class of macrolides, penicillins, cephalosporins, quinolones, aminoglycosides or other antibiotics. Suitably more than one antibiotic can be present. Suitable antibiotics include erythromycin, penicillin, streptomycin, clindamycin, cephalexin, vancomycin, rifampicin. Suitably a tetracycline is not used.

According to a second aspect, there is provided a kit including a container containing the medium according to the first aspect together with a container containing rice starch.

In one embodiment the kit includes a compartmentalized specimen bag. The kit may further include a utensil such as spoon or scoop for transferring a specimen such as faecal matter into the container containing the medium. An additional container may also be provided for containing a specimen.

Suitably the container containing rice starch is a sachet.

According to a third aspect, there is provided a method of detecting the presence of a protozoa in a specimen, said method including:

adding to the medium according to the first aspect, said specimen, rice starch and where necessary, an antibiotic, and allowing the medium to incubate for a time period so as to cultivate protozoa, examining at least a portion of the incubated medium to detect the presence of protozoa.

Suitably the portion examined is or includes sediment.

According to a fourth aspect, there is provided a method of detecting protozoa in faecal matter, said method including:

adding to the medium according to the first aspect, faecal matter, rice starch and where necessary an antibiotic, allowing the medium to incubate for a time period so as to cultivate intestinal protozoa, and examining at least a portion of the incubated medium to detect the presence of said protozoa.

Suitably the portion examined is or includes sediment.

Suitably the protozoa detected are one or more of *Dientamoeba fragilis, Blastocystis hominis, E. histolytica*/dispar, *Iodamoeba butschlii, Endolimax nana, Entamoeba coli,* or

*Entamoeba hartmanni*. Most suitably the protozoa detected is *Dientamoeba fragilis*. Other suitably detected protozoa include protozoa of the genus referred to above, such as *Dientamoeba* spp, *Blastocystis* spp, *Entamoeba* spp or *Iodamoeba* spp. Suitably the portion of the sediment is examined microscopically, although a portion of the sediment can be stained and examined for various protozoa.

In one embodiment the medium is incubated for a period of up to 4 days. In another embodiment the medium is incubated for up to 48 hours. If desired, additional antibiotic and/or rice starch can be added during the incubation period such as after 24 hours of incubation. Suitably the medium is incubated at a temperature of about 36° C. to about 38° C. For example, the temperature may be about 36° C., about 36.5° C., about 37° C., about 37.5° C., or about 38° C. Suitably the antibiotic is one or more antibiotics selected from the antibiotics listed above and is suitably one selected from the group consisting of erythromycin, penicillin, streptomycin, clindamycin, cephalexin, vancomycin and rifampicin.

BRIEF DESCRIPTION OF THE DRAWING

FIG. 1 shows a kit in accordance with one embodiment of the invention.

DESCRIPTION OF PREFERRED EMBODIMENTS OF THE INVENTION

In the present invention the culture method and medium has been simplified to a less complex medium but one that will in use, support the growth of the protozoa referred above including *D. fragilis, Blastocystis hominis* (*B. hominis*) and other parasites including other amoebae (for example, *E. histolytica*/dispar, *Iodamoeba butschlii, Endolimax nana, Entamoeba coli, Entamoeba hartmanni* being other pathogens). The medium in accordance with the invention can double as a transport medium where a sample is taken off-site from the laboratory and then transported to the laboratory. The culture medium preferably uses an egg slope as opposed to previous used saline agar cultures. The egg slope may be made by any appropriate method known in the art, for example by diluting hen's eggs $^{50}/_{50}$ in either Ringer's salt solution or PBS (phosphate buffered saline). The culture medium of the invention demonstrates enhanced reliability of culture. The medium is not as complex as those described in the prior art which comprise numerous chemicals. The medium in accordance with the present invention is—by culture standards—greatly simplified yet more reliable. Unlike the use of live *E. coli* bacteria (which are not suitable to be given to patients in order to collect their own specimens), the medium in accordance with the invention is designed to work even more reliably without *E. coli*.

In addition to the egg or agar slope, the culture medium also contains a liquid phase which includes a serum such as rabbit or horse serum and a peptone such as bactopeptone or bacteriological grade peptone. Typically the liquid phase which is suitably saline and suitably has a pH of from about 6.8 to about 7.8 (more typically about 7.4), contains the peptone in an amount of from about 1 to about 40 vol %, preferably about 20 vol %. Suitably in a 100 mL formulation of the liquid phase, about 1 to 15 mLs, suitably about 5 mLs of the peptone, suitably a bactopeptone solution is used.

The present invention also provides a kit designed to allow a sample such as faecal matter to be placed immediately into the culture medium by the patient. One preferred form of a kit in accordance with the invention is shown in FIG. 1. In FIG. 1, the kit 1 may be in the form of a compartmentalized specimen bag 2 suitably containing four compartments. One compartment contains a specimen container 3 or bottle for collecting a sample such as faeces. A second compartment contains a utensil such as a scoop or spoon 4, suitably a plastic spoon. A third compartment contains a container 5, suitably a sachet containing rice starch. A final container 6 containing the culture medium in accordance with the invention is provided in a fourth compartment.

In use, a patient collects a specimen such as faeces into the container 3. The faecal matter includes for example stool sample, lumina contents or colonoscopy acquired material. A small portion (suitably pea-size) of the specimen is then transferred by means of the scoop 4 and inoculated into the culture medium in container 6. The scoop can either then be discarded or resealed in the second compartment and discarded at the laboratory. Rice starch from container 5 is then added to the medium in container 6. Then, the culture medium is suitably transported to the laboratory for incubation while the protozoa such as *D. fragilis* and other parasites survive the transportation due to the unique nature of the medium which can also double as a transport medium. A "pea-size" amount of stool is required only and it is placed into the culture medium with the contents of the enclosed sachet, added to make the transport/culture simplified. Leftover faecal matter can be used for culture and sensitivity (C & S) and other parasites (parasite OVA).

The culture medium is bi-phasic and consists of a solid phase (the egg and/or agar slope) in a liquid phase. The liquid formulation per 100 mL typically includes about 90 mLs Phosphate Buffered Saline pH 7.4 (suitable range about 6.8-7.8), about 5 mLs of serum, such as sterile horse serum (suitable range about 1-15 mLs) and about 5 mLs 20% of peptone such as bactopeptone (suitable range about 1-15 mLs). Suitably about five drops (suitable range about 1 to 10 drops) of an antibiotic such as about 0.5 wt % erythromycin (suitable range about 0.015 wt % to 30 wt %) is added to the culture medium and a small amount of rice starch, for example, an amount of about 10 mg to about 100 mg, is also added suitably from the sachet. Rice starch is essential for the xenic cultivation of intestinal protozoa (Clark and Diamond 2002—Clark C G, Diamond L S., Methods for the cultivation of luminal parasitic protests of clinical importance. Clinical Microbiology Reviews 2002; 15:329-341). Once the specimen is added to the medium it is incubated at 37° C. for 24 hours suitably in a laboratory (suitably at a temperature in the range of about 36° C. to about 38° C.). Then an extra two drops (suitable range 1 to 5 extra drops) of the antibiotic such as erythromycin are suitably added together with a small amount of rice starch, and a further incubation is suitably carried out for about 24 hours (suitably about 48 hours incubation in total) before examination suitably under a microscope is carried out. Further examinations may be carried out at 3 and finally at 4 days to allow for the occasional detection of slow-growing parasites which may include, for example, one or more of *D. fragilis, B. hominis, E. histolytica*/dispar, *Iodamoeba butschlii, Endolimax nana, Entamoeba coli*, and *Entamoeba hartmanni*. When examined microscopically, a drop of sediment is examined using the ×20 objective of the microscope for the typical morphology of various protozoa. *D. fragilis* ingests the rice starch voraciously, differentiating it-from *B. hominis* when viewed under the microscope. Under microscopic observation, *D. fragilis* appear as round, refractile bodies packed with rice starch. Other intestinal amoebas such as *Entamoeba* and *Iodamoeba* also ingest rice starch, but *D. fragilis* produces characteristic pseudopodia after 10-20 minutes at room temperature. These pseudopodia are leaf-like and are easily distinguishable from those produced by

*Entamoeba*. Positive cultures can be simply confirmed by making a smear of the deposit, allowing it to air dry and fixing it in industrial methylated spirit or ethanol. This then can be stained with Giemsa (10% in PBS (phosphate buffered saline) pH 6.8) for 20 minutes with a wash of buffer before examining under the microscope.

Other parasites and mixed infections may also be detected using the culture method of the invention. Any parasite growing in the culture can be identified by using simple stain. *Entamoeba* sp grow much larger than *D. fragilis* and the pseudopodia are much more obvious and larger. Any query regarding *E. histolytica*/dispar isolates can be resolved by lysing using 0.25 ml 0.25% SDS containing 0.1 M EDTA and conducting a specific PCR/ELISA to confirm/exclude the pathogenic *E. histolytica*. Similarly, *B. hominis* can be detected using this culture. Although the pathogenicity of this parasite is controversial it has been associated with Irritable Bowel Syndrome (IBS). It is possible that a certain subtype of *B. hominis* may be linked with disease, again a lysate can be made and then typed using riboprinting—Clark C G., Riboprinting: a tool for the study of genetic diversity in microorganisms, *J Euk Microbial* 1997; 44: 277-283.

By use of the invention it is possible to detect protozoa including *D. fragilis* in a simple manner.

The invention will now be described with reference to the following examples

CLINICAL EXAMPLES

Example 1

In a 34 yr old female suffering with longstanding loose motions, wind and mild bloating a clinical diagnosis of "Irritable Bowel Syndrome" was made. To exclude enteric parasitic infestation, a stool test was ordered by the patient's physician. A faecal sample was collected by the patient using a small scoop provided in the kit in accordance with one embodiment of the present invention. A pea-sized amount of stool was placed into the culture medium of the invention, which in this case already contained the erythromycin. The contents of a sachet containing rice starch was also added. The specimen was taken to the laboratory where it was incubated for 24 hours at 37° C. A small amount of rice starch was later added as well as 2 drops of erythromycin and the culture incubated a further 24 hours. A drop of the sediment was transferred onto a glass slide and a coverslip added. This preparation was examined under a light microscope using ×20 objective. Round, refractile bodies that had ingested rice starch granules and produced delicate leaf-like pseudopodia after 10-20 minutes at room temperature were identified and a presumptive diagnosis of *D. fragilis* was made. A smear was made, allowed to air-dry, fixed in IMS (industrial methylated spirits) and was simply stained with Giesma for confirmation. The patient was treated with the appropriate anti-parasitic therapy and recovered.

Example 2

In a 49 yr old male patient with a family history of bowel malignancy, complaining of marked flatulence and hepatic flexure cramping pain, a colonoscopy was carried out to exclude the presence of bowel cancer. Simultaneously a sample of lumina contents was collected by aspiration. The colonoscopy acquired material was collected into the specialized faecal container of the invention and a small portion was transferred into the culture medium of the invention. The contents of a sachet provided in the kit in accordance with one embodiment of the invention containing rice starch was also added to the medium. The specimen was transported to the laboratory where it was incubated for 24 hours at 37° C. A further small amount of rice starch was then added together with 2 drops of erythromycin and the culture was incubated for a further 24 hours. A drop of the sediment was transferred onto a glass slide and a cover slip added. This preparation was examined under a light microscope using ×20 objective. Round, refractile bodies that ingest rice starch granules and produce delicate leaf-like pseudopodia after 10-20 minutes at room temperature were detected and a presumptive diagnosis of *D. fragilis* was made. A smear was made, allowed to air-dry, fixed in industrial methylated spirits (IMS) and simply stained with Giemsa for confirmation.

Example 3

A female patient 39 yr of age presented with long standing gastrointestinal symptoms including abdominal pain, flatulence, distention, nausea and minimal weight loss. Repeated faecal samples were negative at the local hospital microbiology laboratory. In the most recent stool sample refractile bodies were observed using direct microscopy, although these could not be identified and did not show up in the parasite concentration method. The laboratory concerned did not use permanent faecal stains, e.g., trichrome or iron-haematoxylin. This is a common feature in Australia and the UK, where very few routine laboratories employ such methodologies. Part of the specimen was transferred into the culture medium of the present invention, using the small scoop provided within the kit of one embodiment of the invention. The contents of a sachet containing rice starch was also added to the medium. The specimen was transported to the laboratory where it was incubated for 24 hours at 37° C. A further small amount of rice starch was then added together with 2 drops of erythromycin and the culture was incubated for a further 24 hours. A drop of the sediment was transferred onto a glass slide and a cover slip added. The preparation was then examined under a light microscope using ×20 objective. Microscopic analysis showed numerous refractile bodies, some of which ingested the rice starch. The Giemsa stain demonstrated the presence of both *D. fragilis* and *B. hominis*, a common finding in patients presenting with IBS-like symptoms.

In the above examples, detection is by standard methods using microscopy with special stains. The components of the formulations used can be sourced from many sources including Sigma Chemicals.

Although the invention is described in terms of various embodiments, it will be readily appreciated by those skilled in the art that various modifications, rearrangements and substitutions can be made without departing from the spirit of the invention.

The claims defining the invention are as follows:
1. A bi-phasic culture medium, comprising:
   a solid phase containing an egg slope or agar slope; and
   a liquid phase consisting of:
      a phosphate buffered saline;
      a serum;
      a peptone; and
      optionally an antibiotic or antibiotics,
   wherein the medium is free of live *E. coli*.
2. The medium of claim 1 wherein the solid phase is an egg slope.
3. The medium of claim 1, wherein the serum is horse serum or rabbit serum.

4. The medium of claim 1, wherein the peptone is peptone or bactopeptone.

5. The medium of claim 1, wherein the phosphate buffered saline has a pH of from about 6.8 to about 7.8.

6. The medium of claim 1, wherein the liquid phase is up to about 98 vol % phosphate buffered saline.

7. The medium of claim 1, wherein the liquid phase contains about 1 to about 15 vol % of serum.

8. The medium of claim 1, wherein the peptone is about 1 to about 40 w/w % bactopeptone solution.

9. The medium of claim 1, wherein the liquid phase contains about 1 to about 15 vol % of the peptone.

10. The medium of claim 1, wherein the liquid phase includes an antibiotic.

11. The medium of claim 10, wherein the antibiotic is selected from among erythromycin, penicillin, streptomycin, clindamycin, cephalexin, vancomycin and rifampicin.

\* \* \* \* \*